United States Patent [19]

Legrand et al.

[11] Patent Number: 4,766,894
[45] Date of Patent: Aug. 30, 1988

[54] PROCESS AND DEVICE FOR SIGNALING MALFUNCTIONS OF A RESPIRATOR

[75] Inventors: Michel Legrand, Lescar; Luc Caillot, Pau; Jean-Michel Donnola, Villecomtal; Roman Siretchi, Pau, all of France

[73] Assignee: Societe Anonyme: M.M.S. s.a. a french corporation, Paris, France

[21] Appl. No.: 37,860

[22] Filed: Apr. 13, 1987

[30] Foreign Application Priority Data

Apr. 15, 1986 [FR] France ................ 86 05382

[51] Int. Cl.$^4$ ............................................. A62B 7/02
[52] U.S. Cl. ........................... 128/204.21; 128/202.22
[58] Field of Search ................ 128/202.22, 204.21

[56] References Cited

U.S. PATENT DOCUMENTS 3,867,934 2/1975 Ollivier .
4,381,774 5/1983 Schreiber et al. .

FOREIGN PATENT DOCUMENTS 2133850 12/1972 France .
2202677 5/1974 France .

Primary Examiner—Gerald A. Michalsky
Attorney, Agent, or Firm—Roberts, Spiecens & Cohen

[57] ABSTRACT

This invention relates to the monitoring of the correct operation of a respirator with single source of energy constituted by a cylinder of pressurized oxygen, to which is annexed a device for connection to a patient. Such monitoring is effected with the aid of a pneumatically operating device which comprises a comparator with adjustable threshold, connected to the mask for connecting to the patient and followed by an amplifier whose output signal takes the binary logic level 1 during the time when the insufflation pressure in the mask is greater than said threshold, and takes the other binary logic level 0 in the opposite case, and a circuit for processing this signal, which triggers off an alarm device if the duration of the time intervals when this latter is at level 1 is too long or too short with respect to a predetermined normal value.

18 Claims, 4 Drawing Sheets

PROCESS AND DEVICE FOR SIGNALING MALFUNCTIONS OF A RESPIRATOR

FIELD OF THE INVENTION

The present invention firstly relates to a process for signaling malfunctions of a respirator or breathing apparatus with a single source of energy constituted by the source of respiratory gas under pressure of the respirator, which makes it possible to apply a pulsatory insufflation pressure to a patient to whom it is connected.

BACKGROUND OF THE INVENTION

At the present time, respirators with double source of energy (electric and pneumatic), principaly used in hospitals, have an alarm system for signaling malfunctions connected either directly with the operation of the respirator, or with physiological disturbances of the patient which prevent him/her from receiving the ventilation furnished by the respirator. This alarm system, most often actuated by a spirometer placed on the patient's breathing circuit, is electronic, the respirator being actuated electrically and/or pneumatically.

On the other hand, up to the present time, emergency respirators with single source of energy, used in ambulances, do not possess an alarm system. The reason for this resides in that, for this type of respirator, it is very important that the alarm system be entirely pneumatic.

SUMMARY OF THE INVENTION

It is an object of the present invention to solve this problem, thanks to a process which essentially consists in comparing with an adjustable threshold value the pulsatory insufflation pressure furnished by the respirator to the patient and in triggering off an alarm if the difference between the maximum value of this pressure and said threshold exceeds a predetermined quantity, either by excess or by want. Any malfunction translated by a cycle of insufflation presenting too high or too low a maximum of pressure may thus be detected and signaled. The process therefore makes it possible to monitor correct functioning of the respirator and its connection circuit to the patient, as well as the correct administration of the breathing gas to said patient.

More particularly, a pneumatic signal formed by pulses which coincide with the periods where the pressure of insufflation is greater than said threshold may be created and the appearance of an excessive difference between the maximum value of this pressure and the above-mentioned threshold may be detected by observing the difference between the value of a representative parameter of said pulses, such as the duration or amplitude thereof, and a predetermined, but adjustable, normal value.

In one embodiment, two distinct pneumatic signals are created from said signal formed by pulses, by subjecting the latter to an integration in two different manners, depending on two respective time constants chosen so that an operation of logic coincidence between these two signals furnishes a result which indicates whether the duration of said pulses is normal, too long or too short. The integration time constants are advantageously such that one of the two resultant signals remains on a determined side of a logic threshold value only when the duration of the pulses is normal or too long, and remains on the other side if this duration is too short, and that the other signal is respectively either on said determined side or on said other side of this logic threshold when the duration of the pulses is either normal or too short, whilst it alternately passes over this threshold when the duration of the pulses is too long.

The invention also relates to a device for carrying out the process defined hereinabove. This device, associated with a respirator with single energy source constituted by the source of respiratory gas under pressure of the respirator, to which is annexed a device for connection to a patient, is entirely composed of pneumatically operating elements and comprises a comparator with adjustable threshold, connected to the device for connection to the patient and followed by an amplifier of which the output signal takes a first binary logic level during the time when the insufflation pressure at the connecting device is greater than said threshold, and takes the other binary logic level in the contrary case, and a circuit for processing this output signal which detects the duration of the time intervals when this latter is at the first level and triggers off an alarm if this duration is too long or too short with respect to a predetermined normal value.

This processing circuit preferably comprises two integrators of which the inputs receive said output signal in common and of which the outputs are connected to the inputs of a logic gate attacking an alarm device, the integrators being designed and adjusted so that the output of the logic gate is at a binary level—continuously or intermittently —triggering off the alarm device when the duration of said time intervals is too long or too short, and at the other binary level, corresponding to the inhibition of the alarm device, when this duration is normal.

Between said logic gate and the alarm device there may be interposed a second logic gate comprising an activation input connected to the pressure source and an inhibition input connected to the output of the first logic gate, which makes it possible to trigger off the alarm device in the case of excessive drop in pressure of said source.

Furthermore, the amplifier which follows the comparator may receive a pulsatory supply pressure synchronized with the insufflation breaths delivered by the respirator, in order to detect any loss of synchronization between the effective ventilation of the patient and the rhythm imposed by the respirator.

At the output of the amplifier there is advantageously connected a pneumatic visual indicator which, by its blinkings, indicates qualitatively the correct functioning of the respirator and, quantitatively, allows initial adjustment of the threshold of the pressure comparator, then monitoring of this adjustment.

BRIEF DESCRIPTION OF THE DRAWINGS

The invention will be more readily understood on reading the following description of non-limiting embodiments, employing, as parameter representative of said pneumatic signal formed by pulses, the duration and amplitude of the latter, respectively, with reference to the accompanying drawings, in which.

DETAILED DESCRIPTION OF THE DRAWINGS

Figure 1:
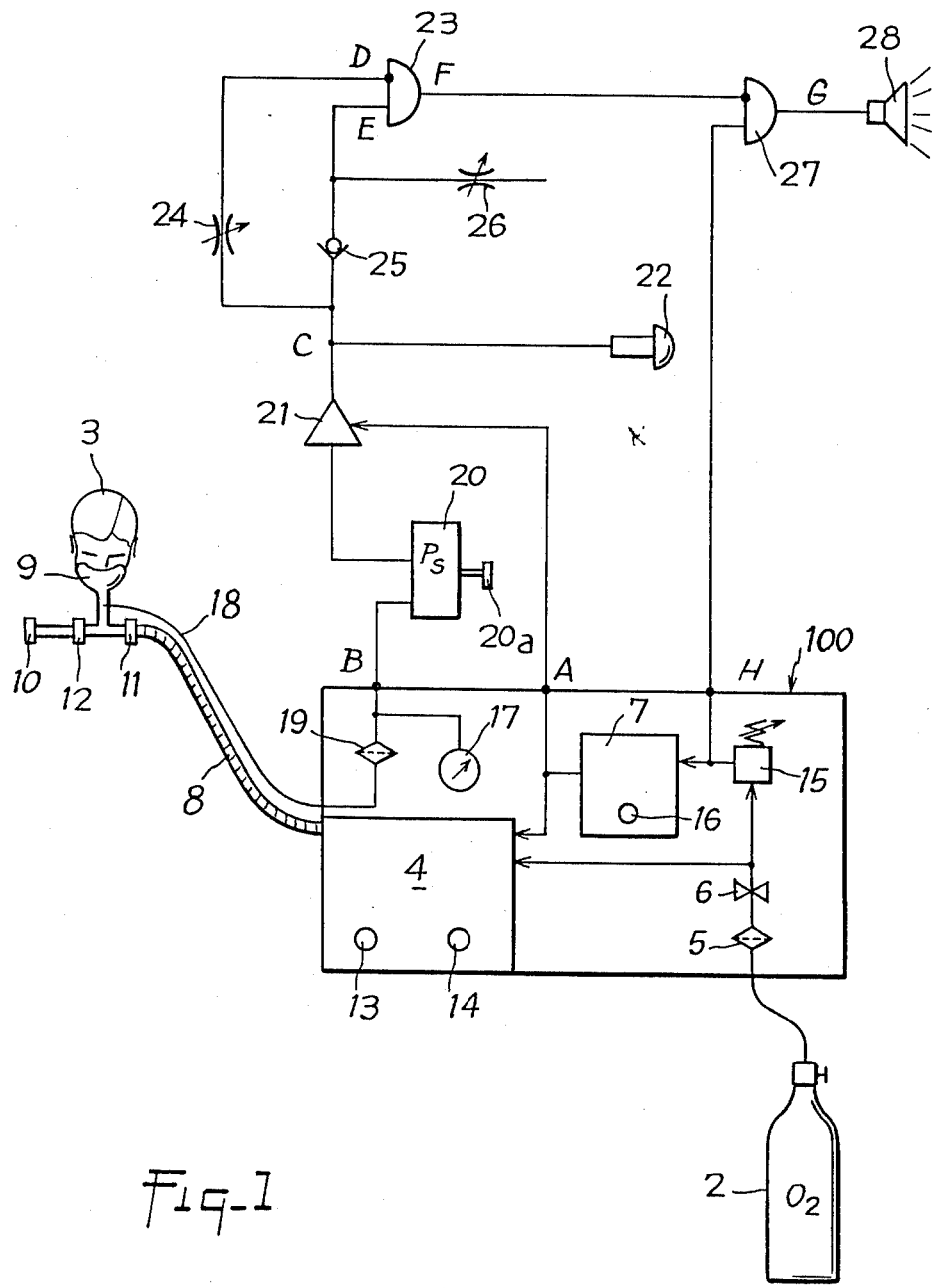
FIG. 1 schematically shows a device according to the invention for monitoring a respirator with single source of energy.

Referring now to the drawings, FIG. 1 shows the principal elements of a respirator 100 using a single energy source constituted by a cylinder of compressed oxygen 2 which supplies the oxygen necessary for the respiratory ventilation of a patient 3.

The respirator 100 comprises a respiratory generator 4 which, supplied with oxygen from the cylinder 2 via a filter 5 and a stop-start valve 6 and controlled by a time base 7, sends breaths of oxygen or a mixture of air/oxygen, at the rhythm of the time base 7, to the patient to whom it is connected by a tube 8 terminating in a mask 9 applied over the patient's face (a tracheal probe with inflatable sealing balloon may also be used for connection to the patient). The mask 9 is also connected to an expiration device 10 making it possible to set a positive expiratory pressure (PEP) greater than atmospheric pressure. Commutation of the gaseous inhalation and expiration flows is ensured by valves 11, 12. A knob 13 makes it possible to adjust the volume of inhalation gas delivered per minute, and another knob 14 makes it possible to choose between pure oxygen and a mixture of air/oxygen.

The time base 7 receives compressed oxygen via a pressure reducing valve 15. It comprises a knob 16 for adjusting the control frequence of the respiratory generator 4.

The pressure of the gas delivered to the patient 3 is measured by means of a pressure gauge 17 connected to the mask 9 by a small auxiliary tube 18, via an anti-bacterial filter 19. At a point B connected to the output of the latter there is therefore available a pressure equal to the pressure prevailing in the patient's mask 9. It is from the parameters of this pressure, varying at the rhythm of the time base 7, that detection is effected of possible malfunctions of the respirator 1, including its elements for connection to the patient.

Figure 2:
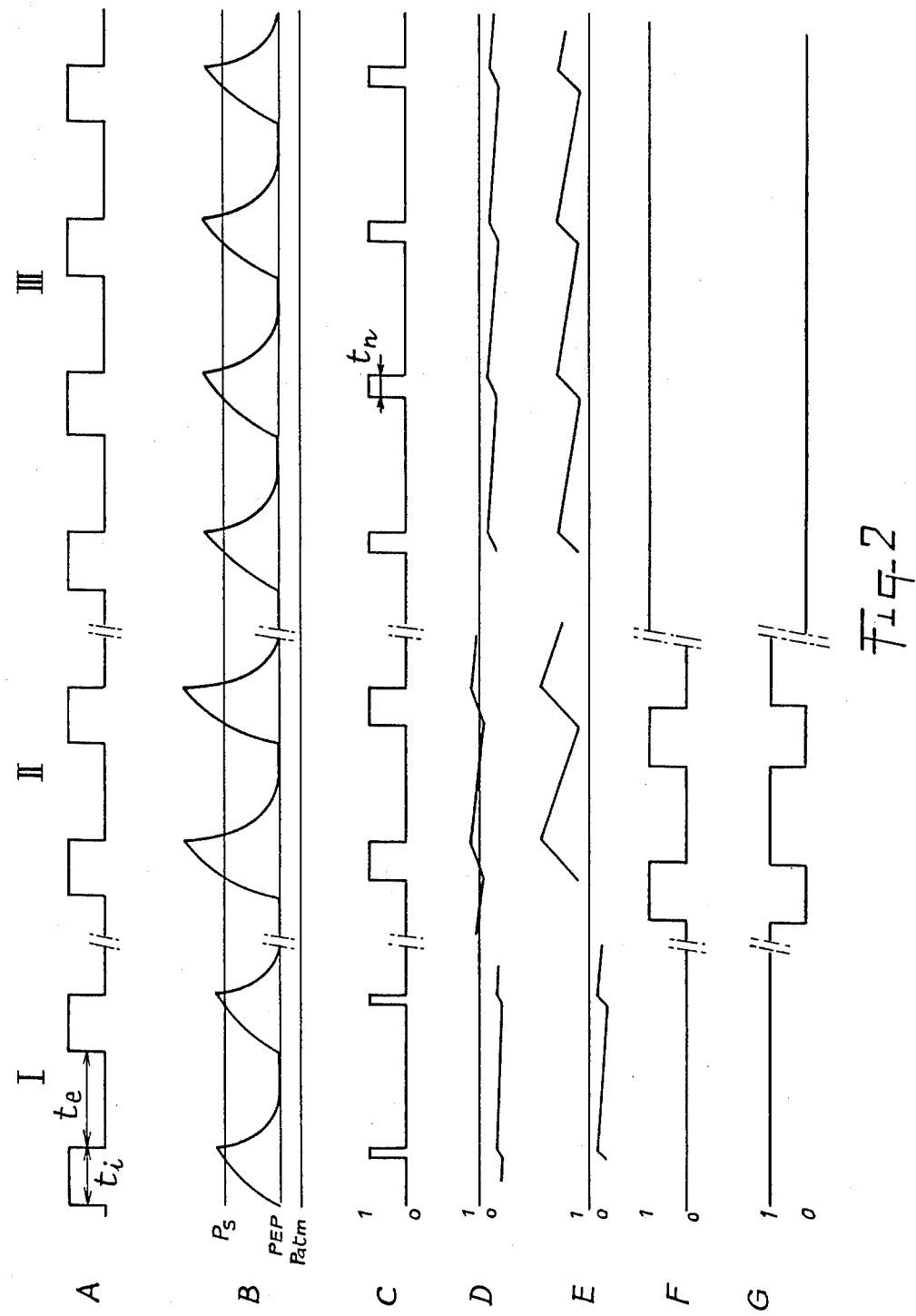
FIG. 2 shows the form of different pneumatic signals which appear in the device of FIG. 1.

FIG. 2A shows the control signal issuing from the time base 7 and available at a point A connected to the output thereof. This signal determines the successive respiratory cycles, composed of a phase of insufflation $t_i$ and a phase of expiration $t_e$. To this pneumatic signal there corresponds the signal available at point B, which represents the variable pressure noted in the patient's mask 9. The form of this signal depends on the possible presence of malfunctions and on the nature thereof. The diagram of FIG. 2 illustrates the influence of two sorts of defect: in case I there is a defect causing an abnormal drop in pressure and, in case II, a defect causing an abnormal excess pressure, whilst case III corresponds to normal operation of the apparatus connected to the patient.

These different cases are distinguished by means of a comparator 20, which receives the pressure signal of point B and compares its maximum amplitude with a pressure threshold $P_s$ adjustable by means of a knob 20a. The comparator 20 delivers pressure pulses during the time intervals when the pressure at point B is greater than threshold $P_s$. These pulses are standardized in an amplifier 21 which delivers at its output C pulses of the same duration, but of constant height (cf. FIG. 2C). It will be noted that the amplifier 21 is supplied not by a pressure of constant value, but by the pneumatic signal issuing from the time base 7 and noted at point A. In this way, said amplifier is validated only during the periods of insufflation $t_i$, with the result that any possible defect in synchronism between the signals of points A and B is manifested in the form of the signal at output C of the amplifier 21 and may consequently be detected.

A pneumatic visual indicator 22 is connected at point C. This indicator blinks during operation, and makes it possible to monitor the existence of the pulsatory signal at that point and to assess its form, more precisely its cyclic ratio, i.e. the ratio of the times when it is at high level (1) and when it is at low level (0). This information helps the operator when adjusting the threshold value $P_s$ of the comparator 20: the durations during which the indicator 22 indicates that the signal of point C is at high level must be neither too long or too short. In practice, they must be of the order of $t_n = 0.2$ second, the exact value depending on the individual patient aided and on his/her state.

The signal of point C is furthermore applied to a circuit for processing by integration, which modifies its form in two different manners, from which result two distinct signals which are applied to the inputs D and E of a pneumatic logic circuit 23. This is a gate which is designed so that only the simultaneous presence of a signal at D at level 0 and of a signal at E at level 1 causes a signal to appear at level 1 at its output F.

A first integration channel, connecting points C and D, comprises a restriction 24. This results at point D (cf. FIG. 2D) in a signal comparable to a signal of level 0 in cases I and III (short and average pulses at point C), and in case II (long pulses), a signal alternately crossing the level of separation of zones 0 and 1.

A second integration channel comprises a non-return valve 25 interposed between points C and E and allowing flow only from C towards E, and a restriction 26 of leakage to the atmosphere, connected to point E. The signal resulting at this latter point (cf. FIG. 2E) is located entirely in zone 0 in the case of case I and entirely in zone 1 in the case of case II or III.

Consequently, the signal which appears at output F of gate 23 (cf. FIG. 2F) is at level 0 in case I, at level 1 in case III and alternately at levels 0 and 1 in case II. This signal is applied to the first input of a logic circuit 27 (similar to circuit 23) of which the second input is connected to a point H from which it receives the supply pressure applied to the input of the time base 7, and which delivers at its output G a signal opposite the signal at point F (cf. FIG. 2G), which energizes a sound alarm device 28 when it is at level 1.

The device described, designed to detect modifications in the ventilation curve (pressure at point B), thus signals, by triggering off a sound alarm —continuous or discontinuous—, the different abnormalities which may occur in the use of the respirator, whether they come from the circuit for connection to the patient or from the respirator itself. Double monitoring is therefore ensured by this device:

(A) Monitoring of the circuit for connection to the patient:

(1) A continuous sound alarm (case I, corresponding to a drop in the maxima of said pressure curve) may signal:
   disconnection of the tube 8;
   crushing or obturation of this tube upstream of valve 11;
   a leakage at the level of the balloon of the tracheal probe used for connection to the patient;

an abnormal reduction of the value of the minimum pressure PEP.

(2) A discontinuous sound alarm (case II, corresponding to a rise in the maxima of the pressure curve) may signal:
an obturation of the tracheal probe;
an abnormal increase in the value of the minimum pressure PEP;
obstruction of the patient's breathing passages.

(B) Monitoring of correct functioning of the respirator
(1) A continuous sound alarm (case I) may signal:
a drop in the supply pressure of the respiratory gas;
a fault in the time base 7;
an obturation of filter 19;
a leakage or disconnection of the pressure indicator tube 18;
a fault in the alarm system (absence of pressure at point F).
(2) A discontinuous sound alarm (case II) may signal:
a fault in the time base 7;
a fault in the bleed-off device with which tube 8 is provided, preventing the expiratory phase.

Figure 3:
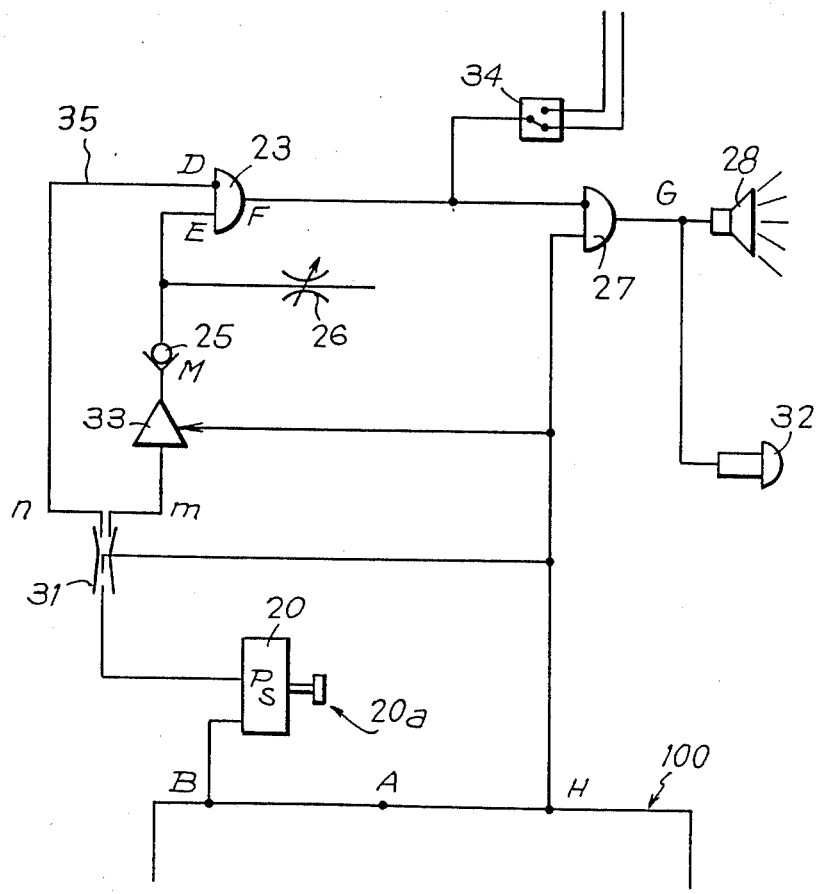
FIGS. 3 and 4 illustrate a variant embodiment and respectively show the pneumatic alarm circuit and the form of the signals which appear therein.

FIG. 3 shows a variant of the pneumatic alarm circuit associated with respirator 100. In this variant, where the signal issuing from point A is no longer used, the comparator 20 is followed by an amplifier with venturi 31 supplied with the fluid under pressure available at point H. The output signal of the amplifier 31 appears split on the two outputs m and n that it comprises, which are connected to the inputs D and E of the gate 23 via two distinct processing channels; the signal of point n is applied directly, via a conduit 35, to point D, whilst the signal of point m is applied to point E via an integration channel similar to that of the device of FIG. 1 comprising the non-return valve 25 in series and the restriction 26 in shunt towards the atmosphere; however, between point m and the valve 25 there is interposed a high-gain amplifier 33, similar to amplifier 21 of the device of FIG. 1, which is supplied with the fluid issing from point H, of constant pressure.

Figure 4:
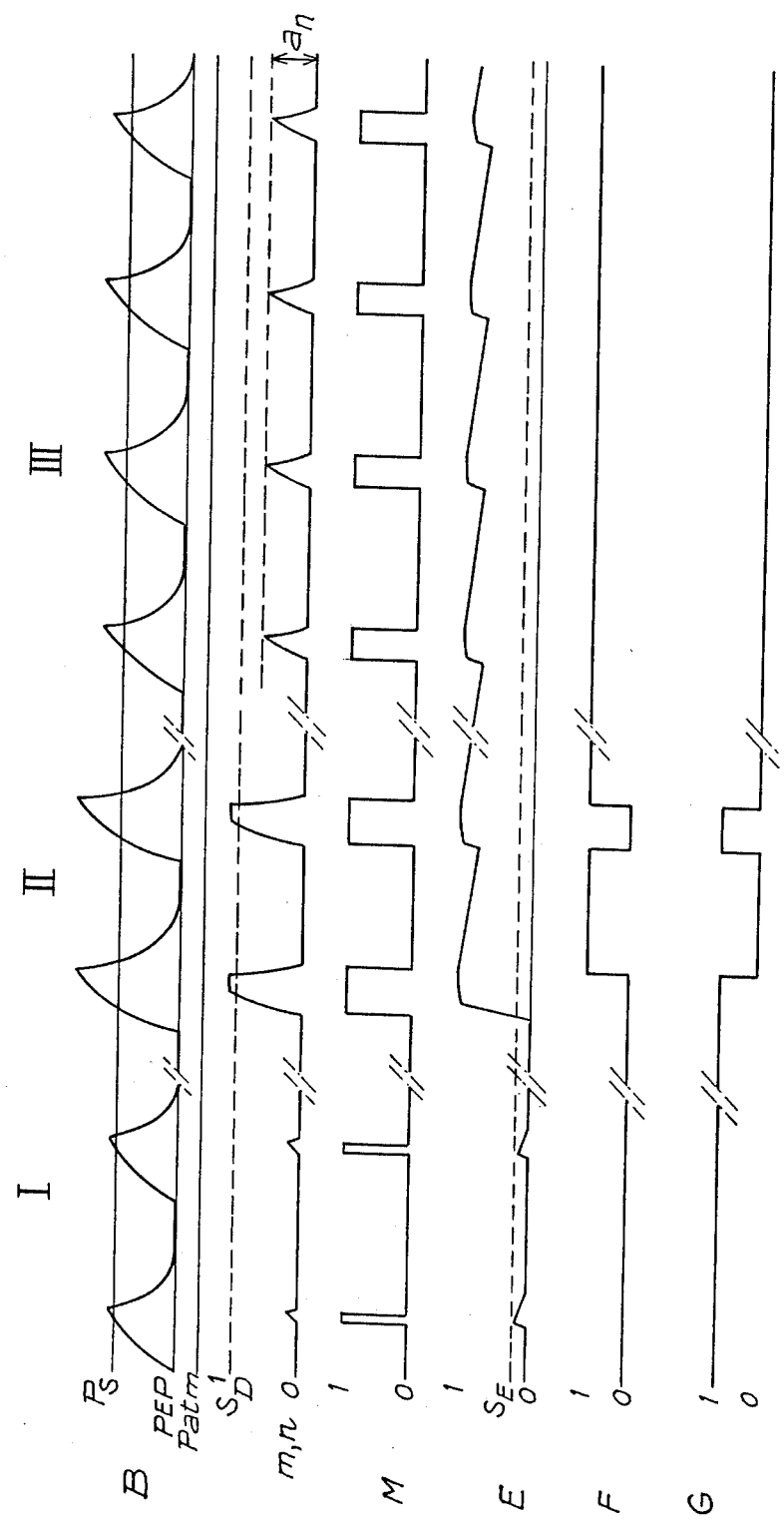

The comparator 20 conserves the same function as before: it delivers pulses during the time intervals when the pressure of point B is greater than threshold $P_s$. Said intervals are applied to the delivery input of the venturi 31, which delivers on its two outputs m, n an amplified signal (cf. FIG. 4). The signal of output m is strongly amplified by amplifier 33, at the output M of which appears a rectangular signal formed by steps at logic levels 0 or 1. This latter signal then undergoes an integration with rapid rise and slow fall and it is the integrated signal which is applied to the input E of gate 23.

In case I where the pressure at point B is too low, the pressure at output n of the venturi 31 is very low. The same applies to the signal appearing at point E, due to the narrowness of these pulses, this signal remaining below the triggering threshold $S_E$ of the input E of gate 23. Consequently, the latter delivers at F a signal at level 0 and an alarm signal at level 1 appears at point G.

On the contrary, if the pressure at point B is too high (case II), the signal at point n exceeds the trigger threshold $S_D$ of the input D of gate 23, whilst the integrated signal at point E becomes and remains clearly greater than the level of threshold $S_E$. An intermittent alarm signal results at the output F of gate 23.

In normal operation, the amplitude of the signal furnished by the venturi 31 is close to the normal value $a_n$, less than the threshold level $S_D$. This signal is therefore too weak to control the input D of the gate 23, whilst the integrated signal applied to the input E remains greater than the threshold $S_E$ thereof (thanks to the high gain of the amplifier 33). Under these conditions, it is a signal at level 1 which appears at the output F of the gate 23, therefore a signal of level 0 at point G, and no alarm signal is emitted.

Another difference of the circuit of FIG. 3 with respect to that of FIG. 1 resides in the mode of connection of the visual indicator used. This indicator, which is referenced 32 here, is connected at point G, in parallel with the sound alarm device 28 and now furnishes a visual alarm, useful in particular in surroundings where the noise level is high. It will be noted that if, in the circuit of FIG. 1, the comparator 20 must be adjusted in order to obtain blinkings of the indicator 22 of short duration, it must now be adjusted in order not to obtain any blinkings of indicator 32.

The circuit of FIG. 3 is completed by a manometric switch 34 whose input is connected to point F. It comprises an electrical contact which changes position when the signal at point F changes logic level. This electrical contact, normally open in the presence of this signal at level 1, may be used for controlling, possibly remotely, an alarm reminder of the respirator. It will be noted that the manometric switch 34 is further capable of detecting and signaling a fault occurring on the pneumatic supply of the respirator (due for example to rupture of the tube for connection to the cylinder of pressurized oxygen), whilst the alarm devices 28, 32 consequently become inoperative.

What is claimed is:

1. A process for signaling malfunctions of a respirator with single source of energy constituted by the source of respiratory gas under pressure of the respirator, which makes it possible to apply a pulsatory insufflation pressure to a patient to whom it is connected, in which said pulsatory insufflation pressure is compared with an adjustable threshold value ($P_s$) and an alarm is triggered off if the difference between the maximum value of this pressure and said threshold exceeds a predetermined quantity either by excess or by want, said process comprising the following steps of:
creating a pneumatic signal formed by pulses which coincide with the periods when the insufflation pressure is greater than said threshold ($P_s$), and
detecting the appearance of an excessive difference between the maximum value of this pressure and the threshold by observing the difference between a representative parameter of said pulses and a predetermined normal value ($t_n$, $a_n$) of this parameter, this value being adjustable.

2. The process of claim 1, wherein two distinct pneumatic signals are created from said signal formed by pulses, by subjecting the latter to a processing in two different manners chosen so that an operation of logic coincidence between these two signals furnishes a result which indicates whether the value of the representative parameter of said pulses is normal, too high or too low.

3. The process of claim 2, wherein there is applied to said signal a processing in two manners such that one of the two resultant signals remains on a determined side (1) of a threshold value only when the value of the parameter of the pulses is normal or too high and remains on the other side (0) if this value is too low, and such that the other signal is respectively either on said determined side (1) or on said other side (0) of this threshold when the value of the parameter of the pulses is either normal or too low, whilst it alternately crosses this threshold when the value of the parameter of the pulses is too high.

4. The process of claim 3, wherein the parameter is the duration of said pulses, which is compared with a predetermined normal duration ($t_n$) of adjustable value.

5. The process of claim 4, wherein the two distinct pneumatic signals are created by subjecting said signal formed by pulses to an integration in two different manners, depending on two respective time constants chosen so that an operation of logic coincidence between these two signals furnishes a result which indicates whether the duration of said pulses is normal, too long or too short.

6. The process of claim 5, wherein the integration time constants are such that one of the two resultant signals remains on a determined side (1) of a logic threshold value only when the duration of the pulses is normal or too long and remains on the other side (0) if this duration is too short, and the other signal is respectively either on said determined side (1) or on said other side (0) of this logic threshold when the duration of the pulses is either normal or too short, whilst it alternately crosses this threshold when the duration of the pulses is too long.

7. The process of claim 3, wherein the parameter is the amplitude of said pulses, which is compared with a predetermined normal amplitude ($a_n$) of adjustable value.

8. The process of claim 7, wherein the two distinct pneumatic signals are created by subjecting said signal formed by pulses to a high amplification, then to an integration depending on a chosen time constant so that an operation of logic coincidence between said signal before amplification and integration and said signal after amplification and integration furnishes a result which indicates whether the amplitude of said pulses is normal, too high or too low.

9. The process of claim 8, wherein the integration time constant is such that one of the two signals remains on a determined side (1) of a first threshold value ($S_E$) only when the amplitude of the pulses is normal or too high and remains on the other side (0) if this amplitude is too low, and the other signal is respectively either on said determined side (1) and exceeds a second threshold value ($S_D$), or on said other side (0) and below this threshold when the amplitude of the pulses is either normal, or too low, whilst it alternately crosses this threshold when the amplitude of the pulses is too high.

10. A device for signaling malfunctions of a respirator with a single source of energy constituted by the source of respiratory gas under pressure of the respirator, to which is annexed a device for connection to a patient, wherein it is entirely composed of pneumatically operating elements and comprises a comparator with adjustable threshold ($P_s$), connected to the device for connection to the patient and followed by an amplifier of which the output signal takes a first binary logic level (1) during the time when the insufflation pressure at the connecting device is higher than said threshold ($P_s$), and takes the other binary logic level (0) in the contrary case, and a circuit for processing this output signal, which detects the duration of the time intervals when the latter is at the first level (1) and triggers off an alarm if this duration is too long or too short with respect to a predetermined normal value.

11. The device of claim 10, wherein the processing circuit comprises two integrators of which the inputs receive said output signal in common and of which the outputs are connected to the inputs of a logic gate attacking an alarm device, the integrators being designed and adjusted so that the output of the logic gate is at a binary level (0)—continuously or intermittently —causing the triggering of the alarm device when the duration of said time intervals is too long or too short, and at the other binary level (1), corresponding to the inhibition of the alarm device, when this duration is normal.

12. The device of claim 10, wherein the amplifier which follows the comparator receives a pulsatory supply pressure synchronized with the insufflation breaths delivered by the respirator.

13. The device of claim 10, wherein a pneumatic visual indicator is connected to the output of the amplifier.

14. A device for signaling malfunctions of a respirator with single source of energy constituted by the source of respiratory gas under pressure of the respirator, to which is annexed a device for connection to a patient, wherein it is entirely composed of pneumatically operating elements and comprises a comparator with adjustable threshold ($P_s$), connected to the device for connection to the patient and followed by an amplifier of which the output signal has a variable amplitude, and a circuit for processing this output signal, which detects the value of the amplitude of this latter with respect to a normal level ($a_n$) and triggers off an alarm if this value is too high or too low with respect to this predetermined normal level.

15. The device of claim 14, wherein the processing circuit comprises a first direct channel and a second high-gain amplification and integration channel of which the inputs receive said output signal in common and of which the outputs are connected to the inputs of a logic gate attacking an alarm device, the two channels being designed and adjusted so that the output of the logic gate is at a binary level (0) —continuously or intermittently—causing triggering of the alarm device when the amplitude of said output signal is too high or too low, and at the other binary level (1), corresponding to the inhibition of the alarm device, when this amplitude is normal.

16. The device of claim 11 or 15, wherein, between said logic gate and the alarm device, there is interposed a second logic gate comprising an activation input connected to the source of pressure and an inhibition input connected to the output of the first logic gate.

17. The device of any one of claims 11 or 15, wherein the alarm device is designed to emit a sound alarm and a pneumatic visual indicator is connected in parallel with said alarm device.

18. The device of any one of claims 11 or 15, wherein a manometric switch is connected to the output of the gate and triggers off an alarm in the event of lack of pressure at this output.

* * * * *